United States Patent [19]

Bobrove

[11] Patent Number: 4,973,317
[45] Date of Patent: Nov. 27, 1990

[54] AUTOMATIC SHEATH PROTECTION OF HYPODERMIC NEEDLE

[76] Inventor: Arthur M. Bobrove, 1539 Walnut Dr., Palo Alto, Calif. 94303

[21] Appl. No.: 379,869

[22] Filed: Jul. 14, 1989

[51] Int. Cl.⁵ .............................................. A61M 5/32
[52] U.S. Cl. ....................................... 604/198; 604/263
[58] Field of Search ............... 604/198, 192, 263, 187, 604/164, 165, 166, 171

[56] References Cited

U.S. PATENT DOCUMENTS 4,846,809 7/1989 Sims ..................................... 604/198
4,850,996 7/1989 Cree ..................................... 604/198

Primary Examiner—John D. Yasko
Attorney, Agent, or Firm—Flehr, Hohbach, Test, Albritton & Herbert

[57] ABSTRACT

Various embodiments of a simple hypodermic needle assembly are described designed to automatically cover the pointed end of the needle after the assembly is used in order to prevent accidental punctures. A sheath circumscribes the needle and includes barbs for interacting with a patient's tissue to cause sliding movement of the sheath over the needle pointed end when the needle is withdrawn from the patient. When the needle pointed end is covered, the barbs automatically withdraw and permit the needle sheath combination to be completely withdrawn from the patient.

15 Claims, 2 Drawing Sheets

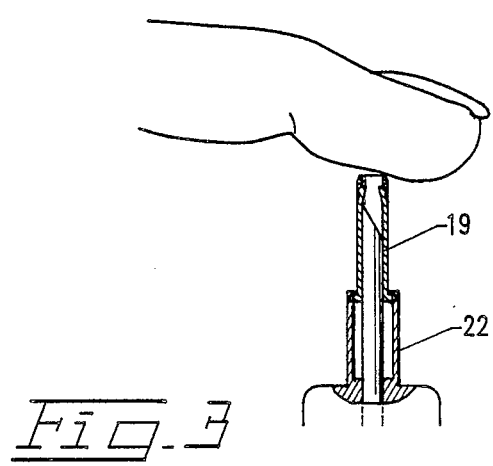
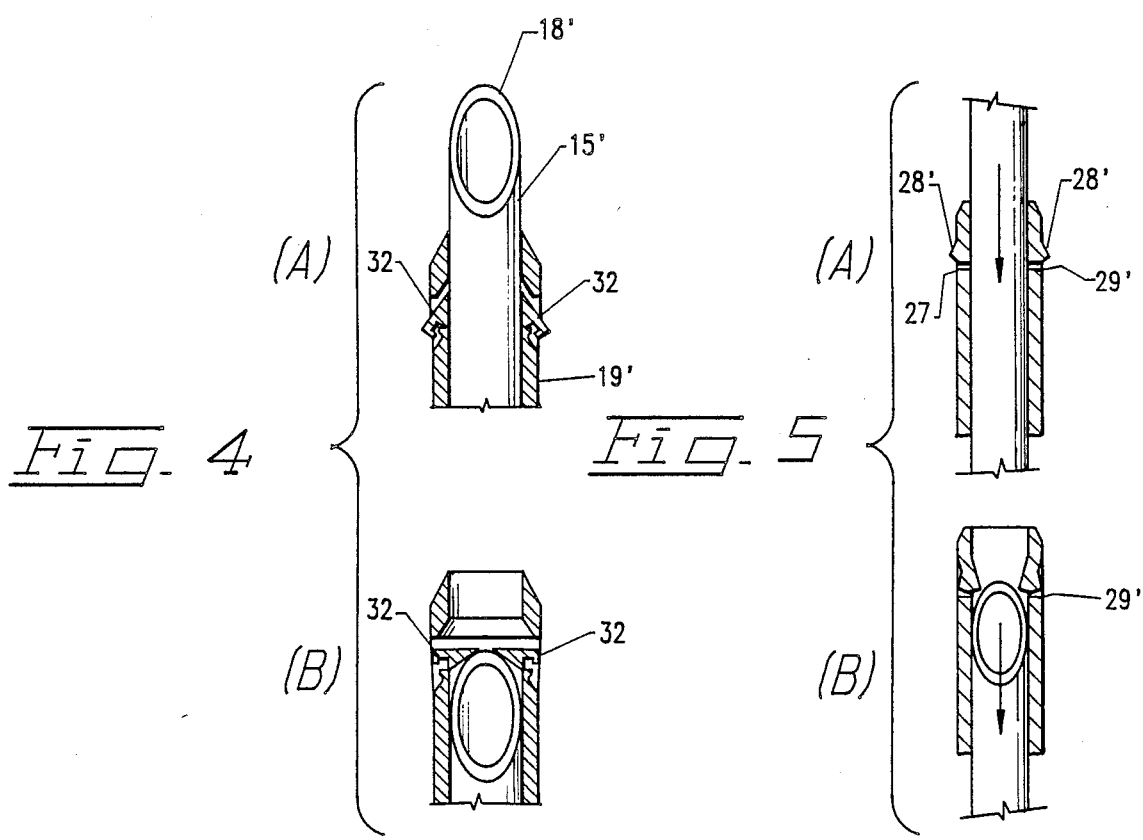

AUTOMATIC SHEATH PROTECTION OF HYPODERMIC NEEDLE

BACKGROUND OF THE INVENTION

This invention relates generally to a protective construction for a pointed end of a medical needle of the type used to pierce the tissue of a patient to inject or withdraw fluid from such patient. More particularly, the present invention is directed to such a construction having a protective sheath which automatically covers the pointed end of the needle when it is extracted from a patient.

Many infectious diseases may be transmitted through an accidental puncture by a contaminated medical needle. This problem is particularly acute with disposable hypodermic needles since they are not sterilized after use and often are not disposed in a manner which will reduce the likelihood of accidental puncture. Since the event of Acquired Immune Deficiency Syndrome (AIDS), increasing concern has developed on the subject of the safety of hypodermic needles.

There have been many designs for shielding the pointed end of a hypodermic needle after use. Many involve manual manipulation to recap the pointed end —some are automatic and thus do not require manual manipulation. Manual capping of a hypodermic needle has many disadvantages. For example, the more one has to manipulate a needle point, the higher the risk of accidental injury. In this connection, with some designs the recapping operation itself can result in an accidental puncture. Moreover, manual manipulation is time consuming. In today's medical environment in which health care workers are already overworked and short in supply, the time spent in recapping a hypodermic needle can be much better utilized on other tasks. Considering the number of times a hypodermic needle is used, the total time spent on recapping hypodermic needles is quite significant. In a sense, that represents an inefficient use of resource. Examples of prior designs which require manual manipulation are described in U.S. Pat. Nos. 3,406,687; 4,681,567; 4,747,837; and 4,801,295.

Past automatic designs, on the other hand, generally are complicated, costly to manufacture, and/or prone to defects. As a general rule, the more complex the design, the more expensive the cost of manufacturing, and the more likely it is that the construction will malfunction. An example of an automatic design is described in U.S. Patent No. 4,775,369.

Some of the above identified problems of automatic type hypodermic needle protective designs are also applicable to those designs requiring manual manipulation. There is much room for improvement. This invention is directed to a substantial improvement in the design of protective constructions for medical needles to reduce the incidence of accidental needle stick injuries.

SUMMARY OF THE INVENTION

The present invention provides a protective construction for a medical needle, particularly a hypodermic needle, which is durable, simple in design, inexpensive to manufacture, and not prone to malfunction. The protective construction includes a sheath which circumscribes the needle in tight-fitting relationship and which has an end portion that penetrates a patient's tissue along with the needle point. In keeping with the invention, the sheath includes a barb or other delaying means which interacts with a patient's tissue such that extraction of the sheath from the patient is postponed to a time no earlier than extraction of the needle point. In that manner, upon extraction of the sheath from the subject, the needle point is automatically covered by the sheath, thus providing a protection against accidental puncture by the needle point after use. Furthermore, such interaction is used to provide the movement necessary to cover the needle point.

As will be described in more detail hereinafter, the invention most desirably also includes a sleeve arrangement which provides a seat for assuring that the sheath follows the needle pointed end in penetrating the patient's tissue. Moreover, most desirably interaction between the sheath and sleeve locks the sheath in position covering the needle pointed end. Other advantages and features of the invention will be described or will become apparent from the following, more detailed description of preferred embodiments.

BRIEF DESCRIPTION OF THE DRAWINGS

With reference to the accompanying two sheets of drawings:

FIG. 3 is a side elevation view illustrating the construction of the preferred embodiment of FIG. 2 protecting a finger from accidental piercing; and FIGS. 4 and 5 are enlarged elevation views of alternative constructions of the barb of the invention.

DETAILED DESCRIPTION OF PREFERRED EMBODIMENTS

Figure 1:
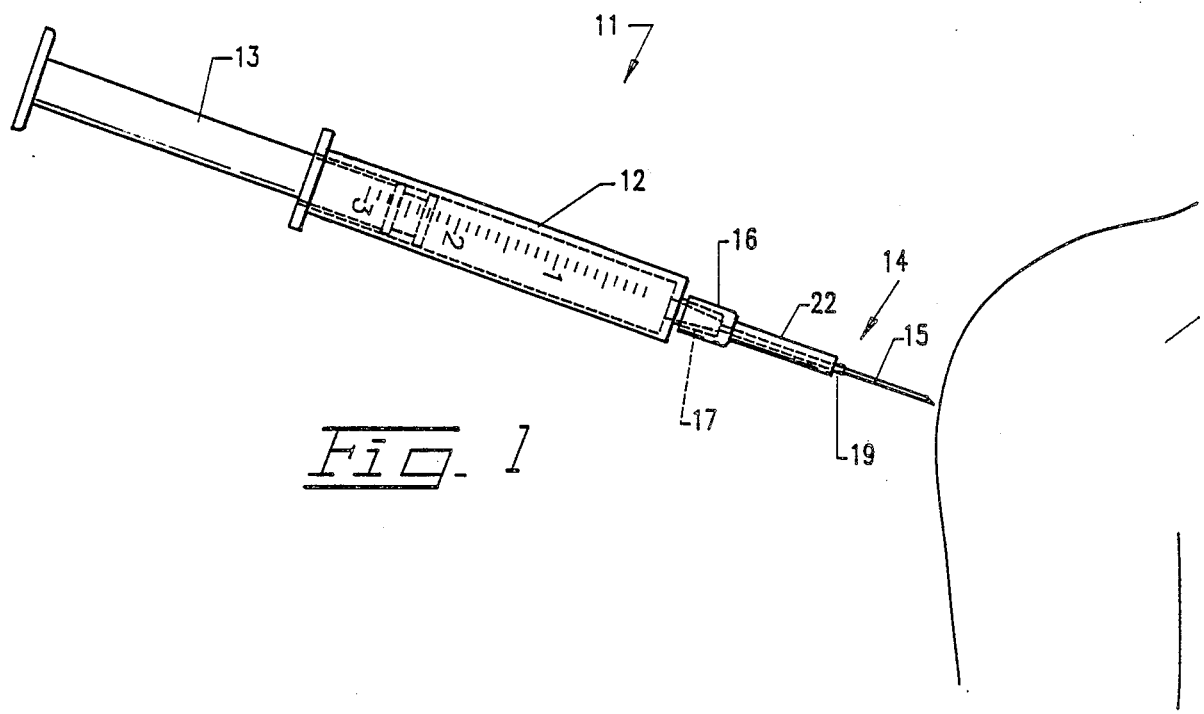
FIG. 1 is an elevation view illustrating a hypodermic needle incorporating the invention poised for piercing the arm tissue of a patient.
Figure 2:
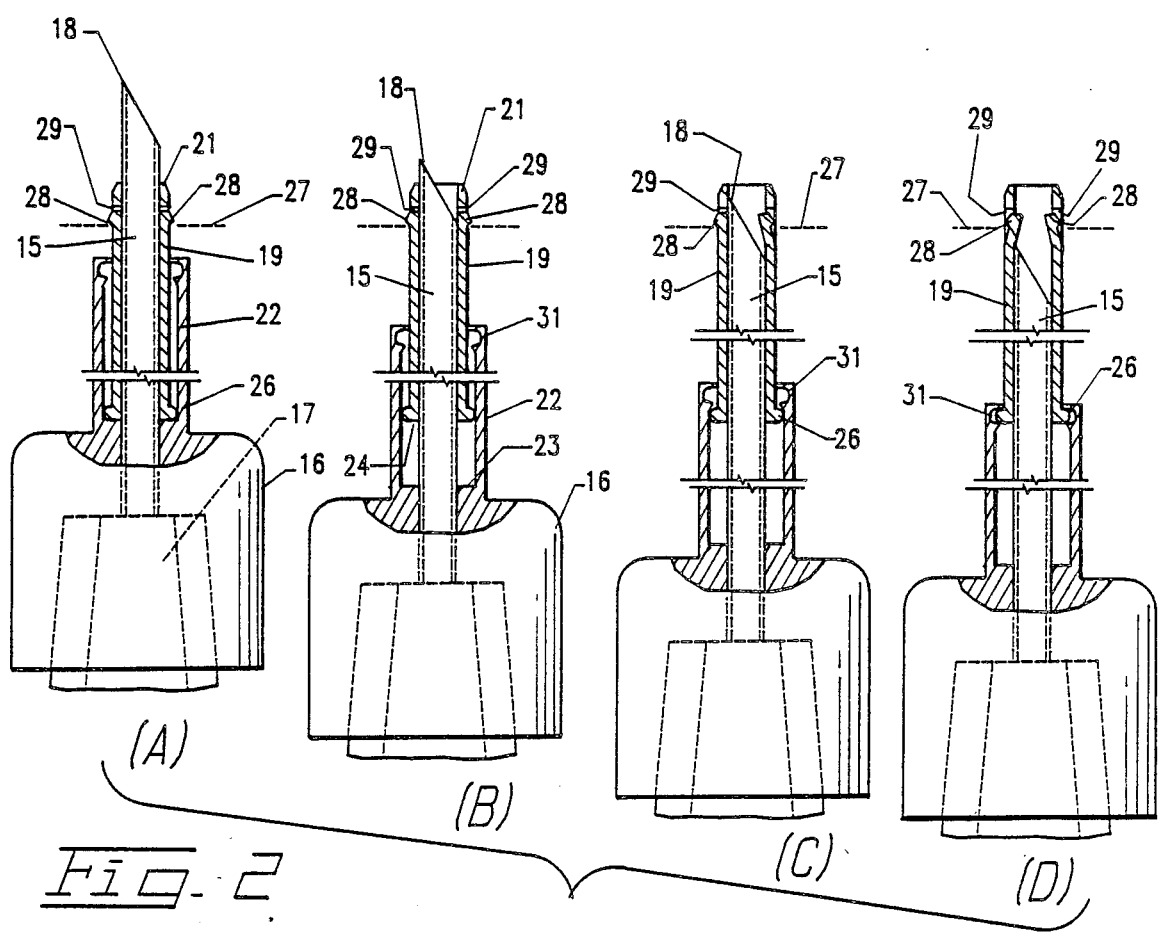
FIGS. 2A-2D illustrate the construction of a preferred embodiment of the instant invention and schematically show its interaction with a patient's tissue.

With reference first to FIGS. 1-3, a generally typical hypodermic needle assembly incorporating the protective construction of the invention is generally referred to by the reference numeral 11. Such assembly includes a hypodermic syringe having a hollow tubular body 12 and a plunger 13 for increasing or decreasing the volume within the syringe which is in communication with a hollow, hypodermic needle construction 14 designed to pierce a patient's tissue. Such construction includes a hollow, stainless steel surgical needle 15. Such construction also includes a hub 16 to facilitate assembly on the hypodermic syringe by insertion of a free end 17 of the syringe into the same for communication with the aforesaid volume. Needle 15 includes a sharpened edge 18 for penetrating the tissue of a patient. Because such needle is hollow, it acts to provide a pathway for fluid being injected into, or withdrawn from, a patient.

In accordance with the invention, a sheath 19 circumscribes the needle in tight fitting relationship with a first end 21 of the same adjacent to the needle pointed end 18. The sheath end 21 is sharpened a small extent to facilitate penetration by it of a patient's tissue with the needle edge 18. It should be noted that the material of the sheath need not be sufficiently structurally rigid in-of-itself to facilitate such penetration—the needle 15 itself will provide the necessary structural strength in view of the close proximity of the same.

The needle construction 14 most desirably also includes a tubular sleeve 22 which circumscribes both the surgical needle 15 and the sheath 19 in spaced relationship thereto as illustrated. Such sheath is mounted on the hub 16 non-movably with respect to the surgical needle 15. It provides a seat 23 to be abutted by the end 24 of the sheath 19 as the needle penetrates a patient's tissue to facilitate penetration also by the sheath. Such end is also provided with an annular ledge 26 for a function to be described.

FIG. 2A represents piercing of a patient's tissue, the perimeter of which is represented at 27. Such penetration is in response to a force applied by the health provider in the direction of the patient's tissue. As illustrated, the sheath 19 follows the surgical needle 15 into such tissue. In this connection, the pointed end 18 provides the initial penetration and leads the way both for the remainder of the needle and the end 21 of the sheath 19. The end 24 of the sheath abuts against seat 23 to assure such penetration. It is important that the longitudinal extent of the sheath along the needle be greater than that of the sleeve 22 to assure penetration of the former without the necessity of the latter also entering the patient's tissue.

In keeping with the invention, means are included on the sheath which interact with the patient's tissue for automatically delaying extraction of the sheath until after extraction of the pointed end from the tissue. A plurality of retractable barbs 28 —(two of which are shown) project radially outward from the sheath 19 to provide such interaction. Each of the barbs is shaped to resist extraction of the sheath when the needle is extracted in response to the normal needle retraction force provided by the health provider. Such retraction is represented in FIGS. 2B and 2C. As illustrated, as the surgical needle 15 is retracted, the sheath retains its position, i.e., the sheath slides on the needle as it is retracted. In this connection, there is sliding movement between a first position as illustrated in FIG. 2 in which the needle pointed end projects beyond the sheath end portion and is exposed, to a second position as illustrated in FIG. 2C in which the needle pointed end is disposed within the sheath. This is accomplished automatically. That is, there is no additional manipulation required by the health provider to cover the needle pointed end.

As a further feature of the instant invention, it includes release means for automatically releasing the barbs 28 from the patient's tissue upon the sheath reaching its covered position. Such release means includes an aperture 29 for each barb extending through the sidewall of the sheath, for its associated barb to enter after the sheath reaches the position in which the needle pointed end is covered. This is represented in FIG. 2D. As illustrated, once the needle passes beyond the interior sidewall of the sheath adjacent the barbs 28, such barbs move inwardly and are withdrawn from the patient's tissue. At the same time the ledge 26 on the distal end of the sheath 19 engages within a detent 31 in the interior wall of the sleeve 22 to adjacent its free end. The surface of the detent 31 and the upper surface of the detent interact to act as a stop to assure withdrawal of the sheath at such time. In this connection, the shape of the barbs 28 is such that force in the extraction direction will cause inward movement of the barbs once the ledge and indent are engaged.

It will be seen from the above that the pointed end of the needle is automatically disposed within the sheath by the needle extraction force. The patient will experience little or no pain because of the penetration by the added sheath and the interaction of the barbs with the patient tissue. A quite efficient and simple means is therefore provided to cover the needle pointed end automatically without any extra manipulation being required by the health provider. It should be noted that the very same forces which traditionally are used by a health provider to both pierce a patient's tissue with a hypodermic needle and extract the same from the patient, are used to provide the automatic disposal of the needle pointed end in the sheath.

FIG. 3 illustrates the manner in which accidental puncture by the needle pointed end is avoided. The material of the sheath relative to the thickness of the same should be selected to resist collapsing to expose the tip of the pointed needle. A suitable material is a tetrafluoroethylene fluorocarbon polymer ('Teflon'). The ledge 26 and indent 31 also provide a lock to assure that the sheath cannot inadvertently be slid along the needle to again expose the needle pointed end. That is, interfering surfaces on the ledge and indent resist such backward sliding movement. Thus, the one construction provides both lock means and stop means. It should be noted that it is not necessary that this stop means and lock means be provided basically at the same location—the reactive forces are in opposite directions. For example, although the ledge 26 could be provided as a symmetrical annular shape as shown, the indent could simply be two stops projecting inward from the sleeve at different longitudinal positions.

FIGS. 4 and 5 illustrate alternate constructions of the barb arrangement and its withdrawal from a patient's tissue. Parts illustrated in these figures which correspond to parts of the embodiment previously described are referred to by the same reference numerals, but primed.

The barb illustrated in FIG. 4 is a fin 32 which is separate from the sidewall of the sheath 19' but is mounted to the sheath for pivotal movement between a projecting position as illustrated in FIG. 4A to a position covering the pointed end of the needle as illustrated in FIG. 4B. In the arrangement illustrated in FIG. 5, the apertures 29' for the barbs 28' are provided in the sheath sidewall toward the hypodermic syringe, i.e., between the needle end point exposed and covered positions. The result is that when the barbs move inwardly in response to the extraction force, such barbs will be in the path of travel of the needle between such positions, abut the needle pointed end, and aid in resisting sliding motion which would expose such pointed end.

Although the invention has been described in connection with preferred embodiments thereof, it will be appreciated by those skilled in the art that various changes and modifications can be made without departing from the spirit of the invention. It is therefore intended that the coverage afforded applicant be limited only by the claims and their equivalents.

What is claimed is:

1. A protective construction for a medical needle having a pointed end for piercing tissue of a patient to inject or withdraw fluid from said patient, said construction automatically providing shielding of said needle pointed end upon extraction of the needle from a patient, comprising:

a sheath circumscribing said needle with a first end portion thereof adjacent to said pointed end for piercing said patient's tissue with said needle in response to a first applied force; and means on said sheath interactive with said patient's tissue for delaying extraction of said sheath in response to a second applied force until after extraction of said pointed end from said tissue;

whereby upon extraction of both said needle pointed end and said sheath from said tissue, said pointed end is automatically disposed within said sheath.

2. A protective construction as recited in claim 1 wherein said needle is a hypodermic needle for a hypodermic syringe having a hollow body containing said fluid.

3. A protective construction as recited in claim 1 wherein said first and second applied forces are respectively also the forces for inserting and withdrawing said needle from a patient's tissue.

4. A protective construction as recited in claim 3 wherein said sheath is mounted on said needle for sliding movement thereon between a first position at which said needle pointed end projects beyond said sheath end portion and is exposed and a second position at which said needle pointed end is disposed within said sheath.

5. A protective construction as recited in claim 4 further including first limiting means for preventing sliding motion of said sheath on said needle beyond said first position so that said sheath travels with said needle in response to said first applied force.

6. A protective construction as recited in claim 5 further comprising:
a sleeve circumscribing said sheath mounted non-movably relative to said needle, and wherein said limiting means is a seat provided by said sleeve for an end of said sheath opposite said first end whereby at said first position said sheath abuts said seat.

7. A protective construction as recited in claim 4 wherein
said delaying means includes a barb projecting from a sidewall of said sheath opposite said needle for interaction with said patient's tissue to move said sheath to said second position in response to said second applied force.

8. A protective construction as in claim 7 further including release means for automatically releasing said barb from said patient's tissue upon said sheath reaching said second position.

9. A protective construction as recited in claim 8 wherein said barb is a separate fin mounted for movement on said sheath between a position projecting from said sheath sidewall opposite said needle for said interaction with said patient's tissue and a position withdrawn from said tissue.

10. A protective construction as recited in claim 8 further including lock means to prevent said sheath from returning toward said first position to expose any needle pointed end after the same is disposed within said sheath.

11. A protective construction as recited in claim 10 further including stop means to assure withdrawal of said sheath from said patient's tissue after said needle pointed end is disposed within said sheath.

12. A protective construction as recited in claim 11 further including a sleeve circumscribing said sheath mounted non-movably relative to said needle, a ledge on one of said sheath and sleeve projecting toward the other, an indent on the other of said sheath and sleeve to receive said ledge when said sheath is in said second position, and interfering surfaces on said ledge and indent providing said lock means and said stop means.

13. A protective construction for a hypodermic assembly needle to inject or withdraw fluid from a patient, said assembly having both a hollow needle having a pointed end for piercing the tissue of a patient and a hollow body for containing said fluid in communication with said needle, said construction automatically providing shielding of said needle pointed end upon extraction of the needle from a patient and characterized by:
a sheath circumscribing said needle with a first end portion thereof for piercing said patient's tissue with said needle in response to a first applied force said sheath being mounted on said needle for sliding movement thereon between a first position at which said needle pointed end projects beyond said sheath end portion and is exposed, and a second position at which said needle pointed end is disposed within said sheath;
a sleeve circumscribing said sheath mounted non-movably relative to said needle;
a seat for an end of said sheath opposite said first end whereby at said first position said sheath abuts said seat;
a barb projecting from a sidewall of said sheath opposite said needle for interaction with said patient's tissue after piercing of the same to move said sheath to said second position in response to a second force applied in a direction opposite to the direction of application of said first applied force; and
whereby upon extraction of both said needle pointed end and said sheath from said tissue, said pointed end is automatically disposed within said tissue.

14. A protective construction as cited in claim 13 further including stop means to insure withdrawal of said sheath from said patient's tissue after said needle pointed end is disposed within said sheath.

15. A protective construction as recited in claim 13 further including lock means to prevent said sheath from returning toward said first position to expose said needle pointed end after the same is disposed within said sheath.

* * * * *